United States Patent
Engel

(10) Patent No.: US 11,884,753 B2
(45) Date of Patent: Jan. 30, 2024

(54) GREEN CATIONIZATION AGENT

(71) Applicant: SACHEM, INC., Austin, TX (US)

(72) Inventor: Tim Engel, Tilburg (NL)

(73) Assignee: SACHEM, INC., Austin, TX (US)

(*) Notice: Subject to any disclaimer, the term of this patent is extended or adjusted under 35 U.S.C. 154(b) by 0 days.

(21) Appl. No.: 17/825,473

(22) Filed: May 26, 2022

(65) Prior Publication Data
US 2022/0403055 A1    Dec. 22, 2022

Related U.S. Application Data

(60) Provisional application No. 63/195,886, filed on Jun. 2, 2021.

(51) Int. Cl.
| | | |
|---|---|---|
| C08B 37/00 | (2006.01) | |
| C07C 227/18 | (2006.01) | |
| C07C 229/12 | (2006.01) | |
| C07D 303/16 | (2006.01) | |

(52) U.S. Cl.
CPC ........ *C08B 37/0096* (2013.01); *C07C 227/18* (2013.01); *C07C 229/12* (2013.01); *C07D 303/16* (2013.01)

(58) Field of Classification Search
CPC . C08B 37/0096; C08B 31/125; C07C 227/18; C07C 229/12; C07D 303/16; C08L 3/08; C08L 5/00
See application file for complete search history.

(56) References Cited

FOREIGN PATENT DOCUMENTS

WO    2004104049 A1    12/2004

OTHER PUBLICATIONS

Bukowska et al., J. Chem. Technol. Biotechnol., 1999, 74, p. 1145-1148. (Year: 1999).*
Henry et al., FEBS Letters, 144, 1982, p. 11-15. (Year: 1982).*
Loonker et al., Afinidad, 2015, 72(571), p. 230-238. (Year: 2015).*
Prado, Hector J. et al., "Cationization of polysaccharides: A path to greener derivatives with many industrial applications", European Polymer Journal, Pergamon Press Ltd Oxford, GB, vol. 52, Dec. 21, 2013, pp. 53-75, XP028609019.
PCT/US2022/031232; PCT International Search Report and Written Opinion of the International Searching Authority dated Sep. 9, 2022.

* cited by examiner

*Primary Examiner* — Jonathan S Lau
(74) *Attorney, Agent, or Firm* — Renner, Otto, Boisselle & Sklar, LLP

(57) ABSTRACT

A compound having Formula (I) or Formula (II):

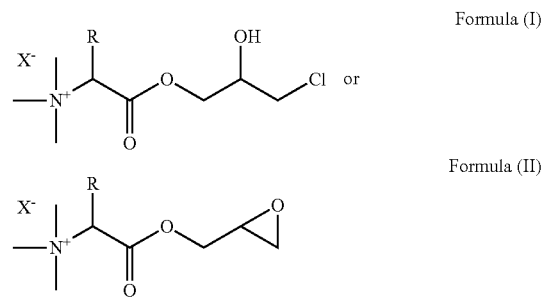

or a mixture thereof,
in which R is —H; —$CH_3$; —CH—$(CH_3)_2$; —$CH_2$—CH—$(CH_3)_2$; —CH—$(CH_3)$—$CH_2$—$CH_3$; —$CH_2$—$(C_6H_5)$; —$CH_2$—(3-indole); —$CH_2$—$CH_2$—S—$CH_3$; —$CH_2$—OH; —CH—$(CH_3)$—OH; —$CH_2$—SH; —$CH_2$-(p-$C_6H_4$OH); —$CH_2$—$CH_2$—$CH_2$—$CH_2$—$NH_2$; —$CH_2$—CO—$NH_2$; —$CH_2$—$CH_2$—CO—$NH_2$; —$CH_2$—$CH_2$—COOH; —$CH_2$—COOH; or —$CH_2$—$CH_2$—NH—C=$NH_2(NH_2)$;
and X is a suitable non-interfering anion, a process for making the compound having Formula (I) or Formula (II), and a process for reacting the compound having Formula (I) or Formula (II) or a mixture thereof with a (poly)saccharide to form a cationized (poly)saccharide.

15 Claims, 4 Drawing Sheets

Thin line: Betaine starting material
Thick line: End product Betaine Reagent

Thin line: un-modified starch
Thick line: modified (isolated) starch with Betaine reagent Thin line: un-modified guar
Thick line: modified (isolated) guar with Betaine reagent

GREEN CATIONIZATION AGENT

RELATED APPLICATION

The present application claims priority to and benefit of U.S. Provisional Application No. 63/195,886, filed 2 Jun. 2021, the entirety of which is hereby incorporated herein by reference.

TECHNICAL FIELD

The present invention relates to the field of cationization agents, in particular, to green cationization agents, and more particularly to green cationization reagents useful for preparation of cationic (poly)saccharides and other cationic substrates, including cationic starches, cationic guar and other cationic cellulosic materials.

BACKGROUND

The cationization of (poly)saccharides and similar target moieties, is well known in the art. As used herein, the terms "target moiety" or "target moieties" refer to the substrate which is being cationized, e.g., a (poly)saccharide. Target moieties, according to the present invention, include (poly)saccharides generally, and especially starches, guar, cellulose and other cellulosic polymers, among others known in the art to be used in forming cationic derivatives of such target moieties.

Cationic (poly)saccharides are used in many different cosmetic formulations. Examples include skincare and haircare (conditioners, leave-on/rinse-off shampoos, styling products, etc.). One of the purposes of cationic (poly)saccharide usage is for improving bonding to hair (scalp and body). Hair naturally has a negative charge and by adding a cationic (poly)saccharide (e.g., cationic starch or cationic guar), this charge is reduced and the product also may form a protective film. Several benefits can be ascribed to this methodology, e.g., improved anti-fizz, color/heat protection, hair strength, suppleness, flexibility, etc.

Cationic (poly)saccharides are effective flocculants and can be used across a wide range of pH. Cationic (poly)saccharides can be used in wastewater purification processes, e.g., to capture and remove inorganic and organic substances having a negative charge. Cationic (poly)saccharides capable of attracting negative charge particles can be very effective sorbents or flocculants in paper and textile industries.

Target moieties, e.g., (poly)saccharides, that can be subjected to cationization include, for example, starch, guar and cellulose, including unmodified and modified forms, such as ethoxylated and/or propoxylated (poly)saccharides. When starch is the target moiety, the starch may be derived from any known source of starch, such as starch from potato, tapioca, or corn.

(Poly)saccharide in native or unmodified form or when oxidized bonds weakly to cellulosic fibers such as cotton and paper. The bonding of (poly)saccharide to cellulosic fiber can be improved significantly by modifying the (poly)saccharide to incorporate cationic groups by cationizing the (poly)saccharide. Cationized (poly)saccharide bonds better to cellulosic fibers by its attraction to the anionic character of the cellulosic fiber. It is noted that, while starch may be the most often herein-referenced target moiety, the principles discussed herein apply generally to (poly)saccharides and to processes for making and using the cationic (poly)saccharides.

The currently available cationization agents are petrochemically based or sourced, which means that the resulting cationic (poly)saccharides used in such formulations are not 100% renewable and sustainable. While (poly)saccharides are generally natural, the cationizing reagents known in the prior art have not been natural or "green". Since today's cosmetic market is focused on natural, renewable and sustainable products, a significant unmet need exists for such products. The present invention has been made to address that need.

An important aspect and a concern within not only the cosmetic industry, but other markets as well, is biodegradability. The need for biodegradability, especially truly natural biodegradability, has increased such that it is now a major concern and an important goal within many industries. The present invention has been made to address that need, too.

In general, in known (poly)saccharide cationization, for example, starch or a starch-containing material is reacted with a dialkyl(epoxyalkyl)amine or trialkyl(epoxyalkyl)ammonium halide, in a medium containing some content of water, and possibly, an organic solvent, in the presence of an alkali metal or alkaline earth metal oxide or hydroxide and other additives. The resulting cationic (poly)saccharide is difficult to break down naturally after use. This difficulty is considered to result from the ether bond between the cationic moiety and the target (poly)saccharide.

In the prior art, various agents have been used for cationization of (poly)saccharides, the most well known being 3-chloro-2-hydroxypropyl trimethylammonium chloride (REAGENS™) or its epoxy analog, glycidyltrimethylammonium chloride (GMAC™). It is noted that 3-chloro-2-hydroxypropyl trimethylammonium chloride is commercially available as Quat-188 or as REAGENS™, which also may be referred to as RCN. Cationic (poly)saccharides may be obtained by an etherification reaction of a starch, for example, a natural potato starch, by treatment with RCN or GMAC™, for example, using NaOH as a catalyst. For example, the reactions may be carried out at temperatures ranging from 35-50° C. for periods of 6-48 hours. These cationic (poly)saccharides, while made from biodegradable (poly)saccharides, are not fully biodegradable due to the strong bond formed between the cationic substituent and the (poly)saccharide target moiety.

There has been a long-standing need in the industry for fully biodegradable, naturally-sourced, "green" cationic (poly)saccharides, made from a "green", renewable, source and having an improved biodegradablility, relative to known cationic (poly)saccharide products. Therefore, a strong interest exists in the market for sustainable, "green", and fully biodegradable (poly)saccharide modifying agents.

As noted above, two of the currently most commonly used agents for modifying target moieties, including starch, guar, and cellulose, are RCN and GMAC™, both of which presently are petrochemically sourced agents. These two agents, referred to above as RCN and GMAC™, have the following structures, shown together with some additional technical information, below each.

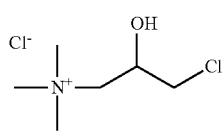

3-chloro-2-hydroxy-N,N,N-trimethylpropan-1-aminium chloride
(RCN, CHPT)
CAS #3327-22-8
$C_6H_{15}Cl_2NO$
Mw: 188,10 g/mol

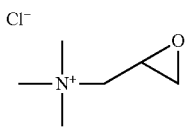

N,N,N-trimethyl-1-(oxiran-2-yl)methanaminium chloride (GMAC™)
CAS #3033-77-0
$C_6H_{14}ClNO$
$M_w$:151,63 g/mol These known cationization agents are not "green" sourced, and are not readily or ultimately, naturally biodegradable. These known cationization agents are derived from non-renewable sources, i.e., primarily from petroleum-based feedstocks. When these current cationizing agents are used in preparing cationic (poly)saccharides, the resulting cationic (poly)saccharides are not readily or fully biodegradable and therefore can persist in the environment for extended periods.

Specifically, though not to be bound by theory, it appears that the bond between the prior art cationic group and the (poly)saccharide is not readily subject to biodegradation. Thus, although the original (poly)saccharide may have been biodegradable, the prior art cationized (poly)saccharides are not readily or fully biodegradable.

As stated above, there has been a long-standing, unmet need for "green", fully biodegradable, and/or naturally-sourced cationization agents for use with (poly)saccharides, such as starches, guar and cellulose.

SUMMARY

The present invention provides such renewable-sourced, more readily biodegradable cationizing agents for preparing cationic (poly)saccharides and other cationic target moieties, including starch, guar, cellulose and other glucose-based materials. It is shown, in accordance with embodiments of the present invention, that incorporating an ester bond into the structure of the cationization agent, will enhance the biodegradability of the product, so that it will be fully biodegradable.

Thus, in one embodiment, the present invention provides a compound having Formula (I) or Formula (II):

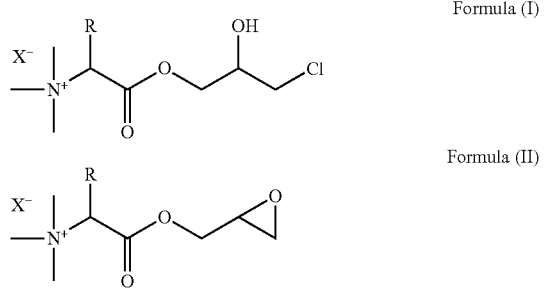

wherein R is —H; —$CH_3$; —CH—$(CH_3)_2$; —$CH_2$—CH—$(CH_3)_2$; —CH—$(CH_3)$—$CH_2$—$CH_3$; —$CH_2$—$(C_6H_5)$; —$CH_2$-(3-indole); —$CH_2$—$CH_2$—S—$CH_3$; —$CH_2$—OH; —CH—$(CH_3)$—OH; —$CH_2$—SH; —$CH_2$-(p-$C_6H_4$OH); —$CH_2$—$CH_2$—$CH_2$—$CH_2$—$NH_2$; —$CH_2$—CO—$NH_2$; —$CH_2$—$CH_2$—CO—$NH_2$; —$CH_2$—$CH_2$—COOH; —$CH_2$—COOH; or —$CH_2$—$CH_2$—NH—C=$NH_2(NH_2)$;

and X is a suitable non-interfering anion. Suitable, non-interfering anions include, but are not limited to, for example, fluoride, chloride, bromide and iodide, acetate, formate, methanesulfonate, and other similar anions.

In one embodiment, R is —H; —$CH_3$; —CH—$(CH_3)$—$CH_2$—$CH_3$; —$CH_2$—CH—$(CH_3)_2$; —CH—$(CH_3)_2$; —$CH_2$—$CH_2$—$CH_2$—$CH_2$—$NH_2$; —$CH_2$—CO—$NH_2$; or —$CH_2$—$CH_2$—CO—$NH_2$; and X is a suitable non-interfering anion.

It is noted that, throughout this disclosure of the present invention, in the structures, e.g., as shown above, for both Formula (I) and Formula (II), the quaternized ammonium N atom is depicted with three methyl groups, for example. In accordance with the present invention, the ammonium N atom may be quaternized with any $C_1$-$C_4$ alkyl group, which preferably is an unbranched $C_1$-$C_4$ alkyl group. The three $C_1$-$C_4$ alkyl groups may be selected independently of each other.

It is noted that, as is well known in the art, a chlorohydrin compound, such as a compound of Formula (I), can be converted into the corresponding epoxy compound, i.e., a compound having Formula (II). Thus, it is understood that, unless otherwise noted, a discussion regarding the cationization of a target moiety by a compound having Formula (I) applies mutatis mutandis to the corresponding compound having Formula (II).

As will be apparent to the skilled person, the R groups in the compounds according to Formula (I) and Formula (II) disclosed herein correspond to the side chain substituents on the natural amino acids. For use in the present invention, these natural amino acids are first quaternized to create the cationic N atom, which is the cationization source for the cationic (poly)saccharides made in accordance with the present invention, prior to reaction with the epichlorohydrin and/or 1,3-dichloro-2-propanol.

Furthermore, the betaine embodiment both corresponds to quaternized glycine and is a naturally occurring compound obtained primarily from sugar beets.

The fact that the ingredients to make the compounds of Formula (I) and Formula (II) are all available from renewable, sustainable natural products, i.e., the natural amino acids, means that the cationization agents of the present invention, i.e., the compounds of Formula (I) and Formula (II), are thus "green", naturally-sourced agents useful for cationization of (poly)saccharides and other similar target moieties. When these cationization agents of the present invention are used with target moieties, including naturally-sourced starches, guar, and other (poly)saccharides, the resulting cationic (poly)saccharides therefore are "green", naturally- and renewably-sourced materials. The resulting cationic (poly)saccharides are more readily biodegradable than are currently known cationic (poly)saccharides made from conventional, prior art, i.e., petrochemical, sources.

It is further noted that, since the preferred amino acids are naturally occurring amino acids, they would be present in the "L" form, rather than the "R" form or a racemic mixture. Thus, the resulting compounds according to Formula (I) and Formula (II) may include an asymmetric carbon atom and thus exhibit some effect on plane polarized light.

The compounds having either Formula (I) or Formula (II) are effective cationizing agents for making cationic (poly)saccharides. The cationization reactions may be carried out similarly to the known cationization reactions using the known prior agents such as the RCN and GMAC™ mentioned above, except that, instead of an ether bond between the cationic group and the saccharide, in the present invention, the bond formed is an ester bond. The presence of the ester bond within the compounds having either Formula (I) or Formula (II) is considered to make the resulting cationic (poly)saccharides more readily biodegradable than prior art products made with prior art starting materials and prior art cationization agents.

The saccharides subject to cationization range from oligosaccharides to (poly)saccharides, and include both homo- and hetero-(poly)saccharides (also referred to as unbranched and branched, respectively), and both modified and non-modified (poly)saccharides. In most instances, the modified (poly)saccharide is modified by treatment with and incorporation of ethoxy and/or propoxy groups, the modified products being referred to as an ethoxylated (poly)saccharide and/or a propoxylated (poly)saccharide. Thus, all of the above variations in the (poly)saccharides and oligosaccharides are within the scope of the present invention.

In one embodiment, the present invention provides a process for producing the compound having Formula (I), the process comprising:
providing a first compound having either Formula (III) or Formula (IIIa):

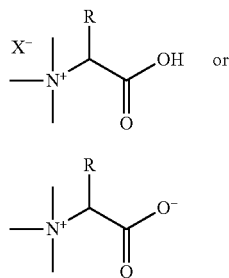

Formula (III)

Formula (IIIa)

wherein R is —H; —CH$_3$; —CH—(CH$_3$)$_2$; —CH$_2$—CH—(CH$_3$)$_2$; —CH—(CH$_3$)—CH$_2$—CH$_3$; —CH$_2$—(C$_6$H$_5$); —CH$_2$-(3-indole); —CH$_2$—CH$_2$—S—CH$_3$; —CH$_2$—OH; —CH—(CH$_3$)—OH; —CH$_2$—SH; —CH$_2$-(p-C$_6$H$_4$OH); —CH$_2$—CH$_2$—CH$_2$—CH$_2$—NH$_2$; —CH$_2$—CO—NH$_2$; —CH$_2$—CH$_2$—CO—NH$_2$; —CH$_2$—CH$_2$—COOH; —CH$_2$—COOH; or —CH$_2$—CH$_2$—NH—C=NH$_2$(NH$_2$); and wherein X is a suitable, non-interfering anion;
providing epichlorohydrin, having formula:

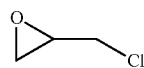

or
providing 1,3-dichloro-2-propanol, having formula:

ClCH$_2$—CH(OH)—CH$_2$Cl or
providing a mixture of both epichlorohydrin and 1,3-dichloro-2-propanol; and
reacting the first compound with the epichlorohydrin or the 1,3-dichloro-2-propanol or the mixture of epichlorohydrin and 1,3-dichloro-2-propanol under suitable esterification conditions to form the compound having Formula (I). Preferably, the various reactants are from natural, renewable, "green", sources.

In one embodiment, the compound having Formula (I) is converted into a compound having Formula (II) by known processes for forming such epoxy compounds from the compounds such as the compound having Formula (I).

In one embodiment, the present invention provides a process for producing the compound having Formula (II), the process comprising:
providing a first compound having either Formula (III) or Formula (IIIa):

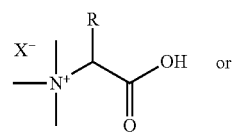

Formula (III)

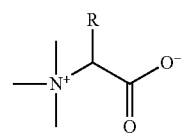

Formula (IIIa)

wherein R is as defined in claim 1,
providing epichlorohydrin, having formula:
or

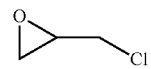

providing 1,3-dichloro-2-propanol, having formula:

ClCH$_2$—CH(OH)—CH$_2$Cl or
providing a mixture of both epichlorohydrin and 1,3-dichloro-2-propanol;
reacting the first compound with the epichlorohydrin or the 1,3-dichloro-2-propanol or the mixture of epichlorohydrin and 1,3-dichloro-2-propanol under suitable esterification conditions to form the compound having Formula (I), and
converting the compound having Formula (I) to the compound having Formula (II) by an epoxidation reaction.

Preferably, the various reactants are from natural, renewable, "green", sources.

It is noted that the initial product formed by either the epichlorohydrin or the 1,3-dichloro-2-propanol is the same, i.e., the compound having Formula (I). This may be converted to the compound having Formula (II) as described herein.

It is noted that epichlorohydrin includes a nonsymmetric carbon atom, and may be present as a racemic mixture of the (+) and (−) enantiomers, and so is properly referred to as (+/−)epichlorohydrin. It is to be understand that reference herein to epichlorohydrin, without more, refers to the racemic mixture (+/−) epichlorohydrin.

It is noted that, where R=H, the compound having Formula (III) corresponds to an HX form of betaine, and if the HX is removed, the zwitterion remaining is the compound known as "betaine". The basic molecule is the amino acid glycine.

It is further noted that when the starting material from which the compound having Formula (III) is made is an amino acid, the amino acid must first be quaternized by a suitable process. In one embodiment, the amino acid is converted to a quaternary ammonium by an Eschweiler-Clarke reaction to form a tertiary amine, followed by alkylation with a suitable alkylating agent, such as methyl chloride, to form the quaternary ammonium derivative of the amino acid.

Thus, for example, if the amino acid used as starting material is valine, in which R=—CH—(CH$_3$)$_2$, a quaternization reaction sequence as shown here would be employed to make the trimethylated valine:

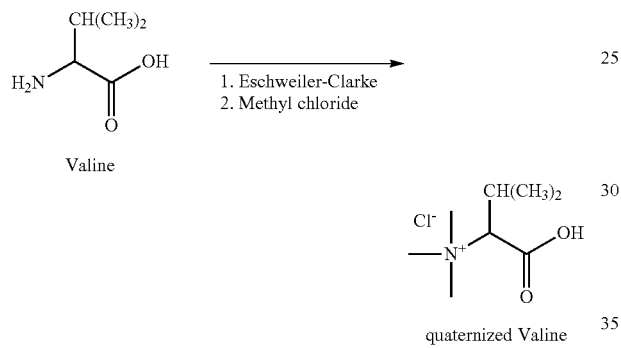

As will be understood, the same basic reaction sequence can be used to prepare the quaternized form of any amino acid, provided that suitable protection can be provided to other possibly reactive moieties in the amino acid of interest. As will be recognized by the skilled artisan, an amino acid with more than one amino group can be singly or doubly quaternized. If singly, then it may be necessary to protect the amino group that is not to be quaternized. Suitable protective groups for amino groups are well known in the chemical arts, and include use of amine-reactive groups such as tert-butyloxycarbonyl ("Boc"), 9-fluorenylmethoxycarbonyl ("Fmoc"), benzyloxycarbonyl ("Cbz"), and allyloxycarbonyl ("Alloc").

As noted above, the ammonium N atom may be quaternized with any $C_1$-$C_4$ alkyl group, and the reagents used in Eschweiler-Clarke reaction and in the final quaternization may be adjusted as needed, depending on the specific alkyl groups selected for the quaternization.

As noted above for Formula (I) and Formula (II), in Formula (III), the ammonium N atom may be quaternized with any independently selected $C_1$-$C_4$ alkyl group, which is preferably an unbranched $C_1$-$C_4$ alkyl group.

In one embodiment, R is —H; —CH$_3$; —CH—(CH$_3$)— CH$_2$—CH$_3$; —CH$_2$—CH—(CH$_3$)$_2$; —CH—(CH$_3$)$_2$; —CH$_2$—CH$_2$—CH$_2$—CH$_2$—NH$_2$; —CH$_2$—CO—NH$_2$; or —CH$_2$—CH$_2$—CO—NH$_2$. These R groups correspond to the more simple amino acids and may be preferred for some applications.

In one embodiment, the present invention provides a cationic (poly)saccharide comprising a reaction product of the compound having the Formula (I) or the compound having the Formula (II) or a mixture of both the compound having Formula (I) and the compound having Formula (II), as described above, with a (poly)saccharide. In one embodiment, the present invention provides a cationic starch comprising a reaction product of a compound having the Formula (I) or the Formula (II) or a mixture thereof with a starch. In one embodiment, the present invention provides a cationic guar comprising a reaction product of a compound having the Formula (I) or the Formula (II) or a mixture thereof with a guar. In one embodiment, the present invention provides a cationic cellulosic polymer comprising a reaction product of a compound having the Formula (I) or the Formula (II) or a mixture thereof with a cellulosic polymer.

In one embodiment, the present invention provides a process for producing a cationic (poly)saccharide comprising:
  providing a suitable (poly)saccharide;
  providing the compound having Formula (I) or the compound having Formula (II) or a mixture of both the compound having Formula (I) and the compound having Formula (II), as defined herein;
  reacting the suitable (poly)saccharide with the compound having Formula (I) or the compound having Formula (II) or the mixture of both the compound having Formula (I) and the compound having Formula (II) under suitable conditions to result in reaction to form the cationic (poly)saccharide.

DETAILED DESCRIPTION

Figure 1:
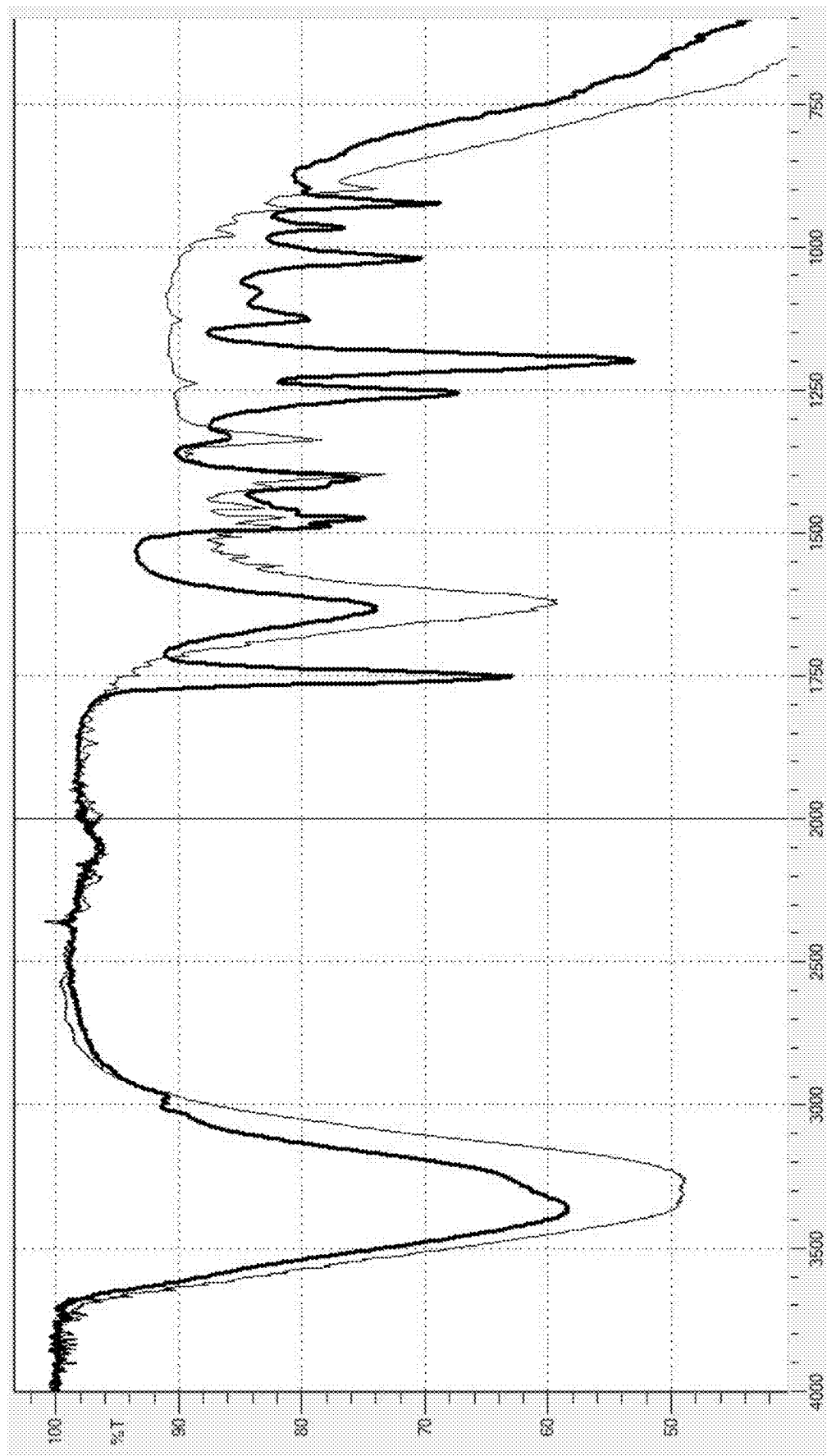
FIG. 1 shows overlapping FTIR scans for betaine and a compound having Formula (I) made from betaine, according to an embodiment of the present invention.

According to embodiments of the present invention, a betaine or betaine-type compound or a quaternized amino acid is used to react with epichlorohydrin, 1,3-dichloro-2-propranol, or a mixture of both, to form an ester linkage between these reactants. The resulting compound, referred to herein as Formula (I) can then be either further treated to form an epoxy group from the chlorohydrin, which forms a compound according to Formula (II); or, alternatively, the Formula (I) compound can be used directly to react with a target moiety, e.g., starch, guar, or other (poly)saccharide, to cationize the target moiety. In the alternate option, if the compound having Formula (II) is formed, the compound having Formula (II) can be used to cationize the target moiety.

In one embodiment, the term "target moiety", singular or plural, does not include surfactants. In one embodiment, the term "target moiety", singular or plural, does not include surfactants or any moieties other than the target moiety(ies) identified positively herein, i.e., (poly)saccharides.

In one embodiment, the present invention begins with a betaine-type or Zwitterionic structure, which may include betaine, betaine HCl, a quaternized amino acid, or a quaternized amino acid hydrogen chloride salt. The betaine-type structure is generalized in the general Formula (III) or the general Formula (IIIa):

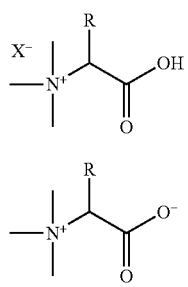

Formula (III)

Formula (IIIa)

wherein, in Formula (III), X is a suitable, non-interfering anion, and R is H or the organic portion of a natural amino acid as defined herein. As will be understood, the Formula (III) moiety is the HX form of the quaternary amino acid or betaine, and the Formula (IIIa) moiety is the free or "natural" form of the quaternary compound of betaine.

It is noted that the term "zwitterion" or "zwitter-ion" only applies to the betaine type compounds herein, since amino acids do not occur naturally as zwitterions.

Where R is H, the compound having Formula (III) or Formula (IIIa) is betaine hydrochloride, or betaine HCl, and as will be understood, where R is H, the underlying amino acid is glycine. This betaine also may be referred to as "glycine betaine".

Where R is the organic portion of an amino acid, R (and corresponding amino acid) may be —$CH_3$ (alanine); —CH—$(CH_3)_2$ (valine); —$CH_2$—CH—$(CH_3)_2$ (leucine); —CH—$(CH_3)$—$CH_2$—$CH_3$ (isoleucine); —$CH_2$—$(C_6H_5)$ (phenylalanine); —$CH_2$-(3-indole) (tryptophan); —$CH_2$—$CH_2$—S—$CH_3$ (methionine); —$CH_2$—OH (serine); —CH—$(CH_3)$—OH (threonine); —$CH_2$—SH (cysteine); —$CH_2$-(p-$C_6H_4$OH) (tyrosine); —$CH_2$—$CH_2$—$CH_2$—$CH_2$—$NH_2$ (lysine); —$CH_2$—CO—$NH_2$ (asparagine); —$CH_2$—$CH_2$—CO—$NH_2$ (glutamine); —$CH_2$—$CH_2$—COOH (glutamic acid); —$CH_2$—COOH (aspartic acid); or —$CH_2$—$CH_2$—NH—C=$NH_2(NH_2)$ (arginine).

In one embodiment, R is —H; —$CH_3$; —CH—$(CH_3)$—$CH_2$—$CH_3$; —$CH_2$—CH—$(CH_3)_2$; —CH—$(CH_3)_2$; —$CH_2$—$CH_2$—$CH_2$—$CH_2$—$NH_2$; —$CH_2$—CO—$NH_2$; or —$CH_2$—$CH_2$—CO—$NH_2$.

Herein, reference to the compound having Formula (III) is considered to include the compound having Formula (IIIa), except if specifically differentiated in the context of the disclosure. For example, since the compound of Formula (III) may be prepared from the compound having Formula (IIIa), simply by forming the HX salt, where X is a suitable non-interfering anion as defined herein, they may be considered for many purposes the same compound, especially in solution or in a reaction.

As noted above for all the compounds according to Formula (I), Formula (II), Formula (III) and Formula (IIIa), the ammonium N atom may be quaternized with any independently selected $C_1$-$C_4$ alkyl group, which is preferably unbranched.

The compound having Formula (III) may be reacted with epichlorohydrin:

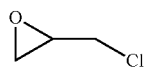

such that the acid portion of the compound of Formula (III) reacts under suitable conditions with epichlorohydrin to form the compound of Formula (I), as shown in the following:

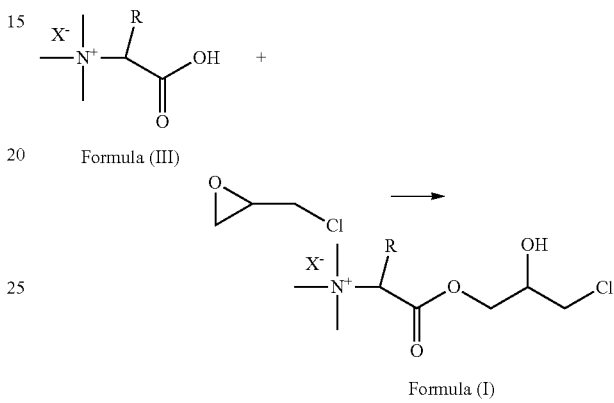

Formula (I)

using known reaction conditions. Such known reaction conditions include, for example, acid-catalyzed esterification reaction between the compound having Formula (III) and epichlorohydrin, and may also be carried out between the compound having Formula (III) and 1,2-dichloro-2-propanol. This reaction may be conducted, for example, at elevated temperature, with or without elevated or reduced pressure. Other known esterification conditions may be applied as suitable.

In one embodiment, the chlorohydrin ester, having general Formula (I) shown above, may be converted into the epoxy analog by known procedures. A known procedure for converting a chlorohydrin to the epoxy analog is to heat the chlorohydrin in the presence of an organic co-solvent and a base, such as sodium hydroxide or an organic base, to form the epoxy analog, sodium chloride and water.

In accordance with the present invention, the compound having Formula (I) is converted into the compound having Formula (II) by reaction under such pH regulated conditions of alkali hydroxide or organic base and heat.

By virtue of the ester linkage, this cationization agent, when used to form a cationic (poly)saccharide, produces a cationic (poly)saccharide that is readily biodegradable. Cationization of other suitable target moieties produces biodegradable products, as well, for the same reason—that is, it includes the ester portion of the product molecule, which is considered to enable ready biodegradation through hydrolysis of the ester moiety.

The compounds having Formula (I) or Formula (II) are used, in accordance with the present invention, to form a cationic (poly)saccharide or other cationic target moiety, such as cationic starch, cationic guar, or a cationic cellulose polymer.

Depicted below are examples of a cationic (poly)saccharide made according to the prior art, and a cationic (poly)saccharide made in accordance with the present invention, both using a starch backbone as example. The distinction that provides biodegradability is considered to be the ester linkage in the (poly)saccharide made according to the present invention. As defined herein, X is a suitable, non-interfering anion.

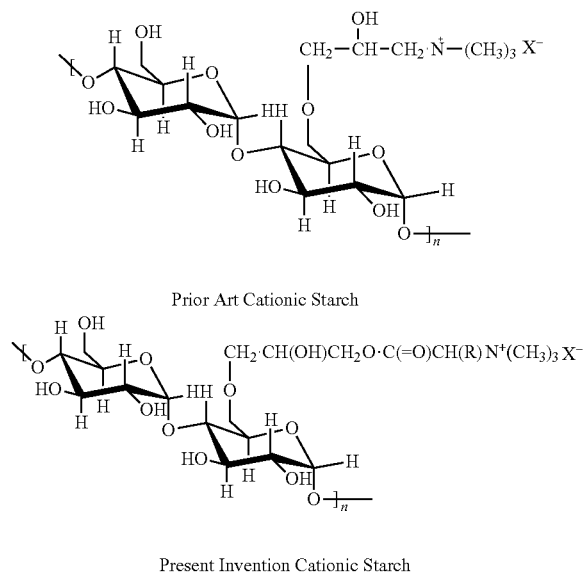

Prior Art Cationic Starch

Present Invention Cationic Starch

In both of these example cationic starches, the cationizing agent has bonded to the starch via the 6-position oxygen atom on the glucose ring in the starch molecule depicted here. It is the presence of the ester linkage in the present invention cationic (poly)saccharide that is considered both novel and inventive and to render the resulting cationic starch biodegradable, in accordance with embodiments of the present invention.

As described herein, in the cationic (poly)saccharide, and other target moieties, made according to the present invention, R and X are as described in the foregoing descriptions.

The cationization reaction is carried out as needed to obtain the desired degree of substitution (DS) in the cationic (poly)saccharide product. As known in the art, various DS may be sought as appropriate, depending on, e.g., the intended use of the cationic (poly)saccharide.

EXPERIMENTAL

Preparation of Betaine*HCl salt solution

Pre-charge reactor with water and slowly add solid Betaine (preferred concentration of solution 20-40%). Slowly add one molar equivalent of HCl solution (35-37% concentration), keeping temperature between 20-30° C. 30 minutes after addition of the HCl solution, the aqueous solution containing Betaine*HCl can either be used directly or isolated in solid form via distillation. Isolated solid Betaine*HCl is redissolved in a polar solvent (preferably, a polar protic solvent).

Betaine Cationic Reagent

Based Upon Aqueous Betaine*HCl Solution

Pre-charge reactor with a 1 to 5 molar excess of epichlorohydrin, based upon the amount of betaine*HCl to be used. Increase temperature to 40-120° C. (preferred, 60° C.-105° C.).

Slowly add the previously prepared Betaine*HCl solution over a 2 hour period.

Allow reaction time of 3 hours at these conditions.

Then, reduce the temperature of the reaction mixture to 20-25° C.

Measure pH level and adjust pH level appropriately. pH level adjustment depends on the desired product.

2-(3-chloro-2-hydroxypropoxy)-N,N,N-trimethyl-2-oxoethanaminium chloride

Betaine (REAGENS™) solution pH level is adjusted to pH5-pH7 (preferred is pH 6) via slow addition of a diluted HCl solution (for example, preferably 5% HCl solution).

N,N,N-trimethyl-2-(oxiran-2-ylmethoxy)-2-oxoethanaminium chloride (betaine 'GMAC')

Extra attention should be applied for reducing the possibility of hydrolysis. Initially a measurement is done on the hydrolysable chloride content and HPLC analysis. Based upon ascertained results, calculated amount (1 to 1 ratio) of a dilute base (NaOH or organic base), which is slowly added under continuous temperature and pH monitoring, keeping pH level 8-10 during the addition and at a temperature 20-50° C.

Product Work-Up

Conduct phase separation and isolate the aqueous layer (=product stream). The aqueous solution containing the betaine cationic reagent is further purified, removing present organic impurities (e.g., epichlorohydrin, 1,2-dichloropropanol and 1,3-dichloropropanol) by multiple extraction/washing steps with a polar aprotic solvent (for example, methylethylketone is preferred).

After the purification step, residual trace amounts of the extraction solvent are removed via vacuum distillation.

Betaine Cationic Reagent Via Betaine Directly

Prepare a solution of betaine by dissolving the reactant in a polar solvent (preferably, a polar protic solvent).

Pre-charge reactor with a 1 to 10 molar excess of either (±)epichlorohydrin or 1,3-dichloro-2-propanol, based upon the amount of betaine used.

Increase temperature to 60° C. and slowly add the solution containing betaine to the reactor.

After addition, reaction temperature is increased to 90-150° C. (preferably 110° C.). Let reaction mixture stir at set conditions for 8-24 hours (preferably 8 hours). After reaction, pH level is measured and adjusted or maintained to pH 5-pH 7 (preferred pH 6) using, e.g., dilute HCl solution.

Product Work-Up

Similar to the example using Betaine*HCl, organic impurities formed (e.g., epichlorohydrin, 1,2-dichloropropanol and 1,3-dichloropropanol) are removed by multiple extraction/washing steps with a polar aprotic solvent (methylethylketone may be preferred).

After the purification step, residual trace amounts of the extraction solvent are removed via vacuum distillation.

Amino Acid Based Cationic Reagents

Cationic reagents based upon amino acids are prepared by a two step reaction. Initially the present amine groups are converted to tertiary ammonium groups by means of the Eschweiler-Clarke route. As noted, if multiple amine groups are present, any amine not to be reacted should be protected, as known in the art, prior to further steps. Taking 2-aminopropanoic acid (alanine) as an example, 2-aminopropanoic acid reacts with formalin (=aqueous solution of formaldehyde) to form an imine. Following the formation of the imine, formic acid is added to protonate the imine, thereby forming the secondary amine and carbon dioxide. This process is repeated once more, to provide the tertiary amine. Typical reaction temperature is 40-120° C.

This newly formed tertiary amine is quaternized by means of dosing with, e.g., methyl chloride gas, or other alkyl halide as appropriate, in the presence of a polar aprotic solvent (preferred solvent, acetonitrile).

The formed product, 1-carboxy-N,N,N-trimethylethanaminium chloride, having the structure shown below, is brought into water via a solvent switch.

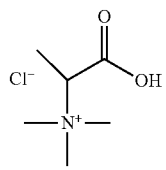

1-carboxy-N,N,N-trimethylethanaminium chloride

The second step in the process is similar to the process described above using Betaine:

Prepare a solution of the quaternized amino acid (in this example, 1-carboxy-N,N,N-trimethylethanaminium chloride) by dissolving the it in a polar solvent (preferably, a polar protic solvent, e.g., water).

Pre-charge the reactor with a 1 to 10 molar excess of either (±)epichlorohydrin or 1,3-dichloro-2-propanol, based upon the amount of quaternized amino acid used. Increase temperature to 60° C. and slowly add the solution containing the quaternized amino acid to the reactor.

After addition, reaction temperature is increased to 90-150° C. (preferably 110° C.).

Allow the reaction mixture stir at set conditions for 8-24 hours (preferably 8 hours).

After the reaction mixture is stirred for the above time, the pH level is measured and adjusted or is maintained to pH 5-pH 7 (preferred pH 6) using, e.g., dilute HCl solution.

Product Work-Up

The organic impurities present in the aqueous reaction solution (e.g., epichlorohydrin, 1,2-dichloropropanol and/or 1,3-dichloropropanol) are removed by multiple extraction/washing steps with a polar aprotic solvent (preferred, e.g., methylethylketone). After the purification step, residual trace amounts of the extraction solvent are removed via vacuum distillation.

Example Process for Cationization of a (Poly)Saccharide

Pre-charge a reactor with solvent (water, isopropyl alcohol, acetone or a combination thereof); add appropriate amount of selected (poly)saccharide.

Increase temperature to the range of 30-50° C. (preferred temperature is 37.5° C.)

Add appropriate amount of sodium hydroxide (preferably a 5% solution) to obtain pH 9-11 (preferred is pH 10.5).

Allow reaction mixture to stir for 1-3 hours at these conditions.

Slowly add an appropriate amount of the cationic reagent according to Formula (I) or Formula (II). The appropriate amount is based on the selected, desired DS value in the cationized (poly)saccharide product. This amount can be readily determined by the skilled person.

Let reaction mixture stir for 1-3 hours at set conditions.

Measure pH level and, if needed, adjust to pH 8-10 (preferred is pH 9).

Let reaction mixture stir at set conditions for 4-24 hours (preferred, 24 hours) Lower temperature to about 24° C.

Adjust pH level to pH 5-7 (preferred is pH 6.5)

Isolated cationic (poly)saccharide via vacuum filtration and wash three times with demineralized water or solvent (e.g. acetone or isopropyl alcohol)

Dry obtained cationic (poly)saccharide via vacuum distillation or oven to remove residual solvent.

Example of a Shampoo Formulation Using Cationic Guar

The cationic guar, made by a process in accordance with the present invention, is the first ingredient introduced in the shampoo preparation, i.e., prior to the surfactants and other ingredients. The following steps, in order:

With moderate agitation, slowly add the cationic guar into water with a propeller mixer. Continue to mix during 10 to 15 minutes until homogeneous.

Adjust pH to 3-4 with lactic or citric acid before addition of high pH surfactant.

First add the amphoteric and/or nonionic surfactants if present. Mix until homogeneous.

Then add slowly the anionic surfactant with mixing. Mix until homogeneous.

Add the remaining ingredients (preservatives, perfume, etc.)

Add NaCl to adjust the final viscosity. Mix until homogeneous

It is important to first add the amphoteric surfactants and then the anionic surfactants to avoid compatibility issues.

Example of a Shampoo Formulation

| INGREDIENT | % w/w (AM) |
| --- | --- |
| Water | QS to volume |
| Sodium coco sulfate | 6.00 |
| Cationic (poly)saccharide | 0.50 |
| Lauryl glucoside | 4.00 |
| Coco glucoside | 2.50 |
| Glycerin | 3.00 |
| Preservatives | 0.60 |
| Lactic Acid | to pH 5.5-6.0 |
| Sodium Chloride | 1.50 |

(Note: coco is a mixture of fatty acids from coconut oil.)

The figures include FTIR scans comparing starting materials and reaction products to show evidence of the formation of the reaction products, and mass spectrum to show the molecular weight of the betaine-source cationizing agent, in accordance with embodiments of the present invention. Each figure is briefly described in the following paragraphs.

FIG. 1 shows overlapping FTIR scans for betaine and a compound having Formula (I) made from betaine, according to an embodiment of the present invention. The differences in the IR peaks show the characteristic peaks for the compound having Formula (I), as compared to the IR peaks for the unreacted betaine. It is noted, for example, that the peak at about 1750 cm$^{-1}$ would correspond to the ester carbonyl group.

Figure 2:
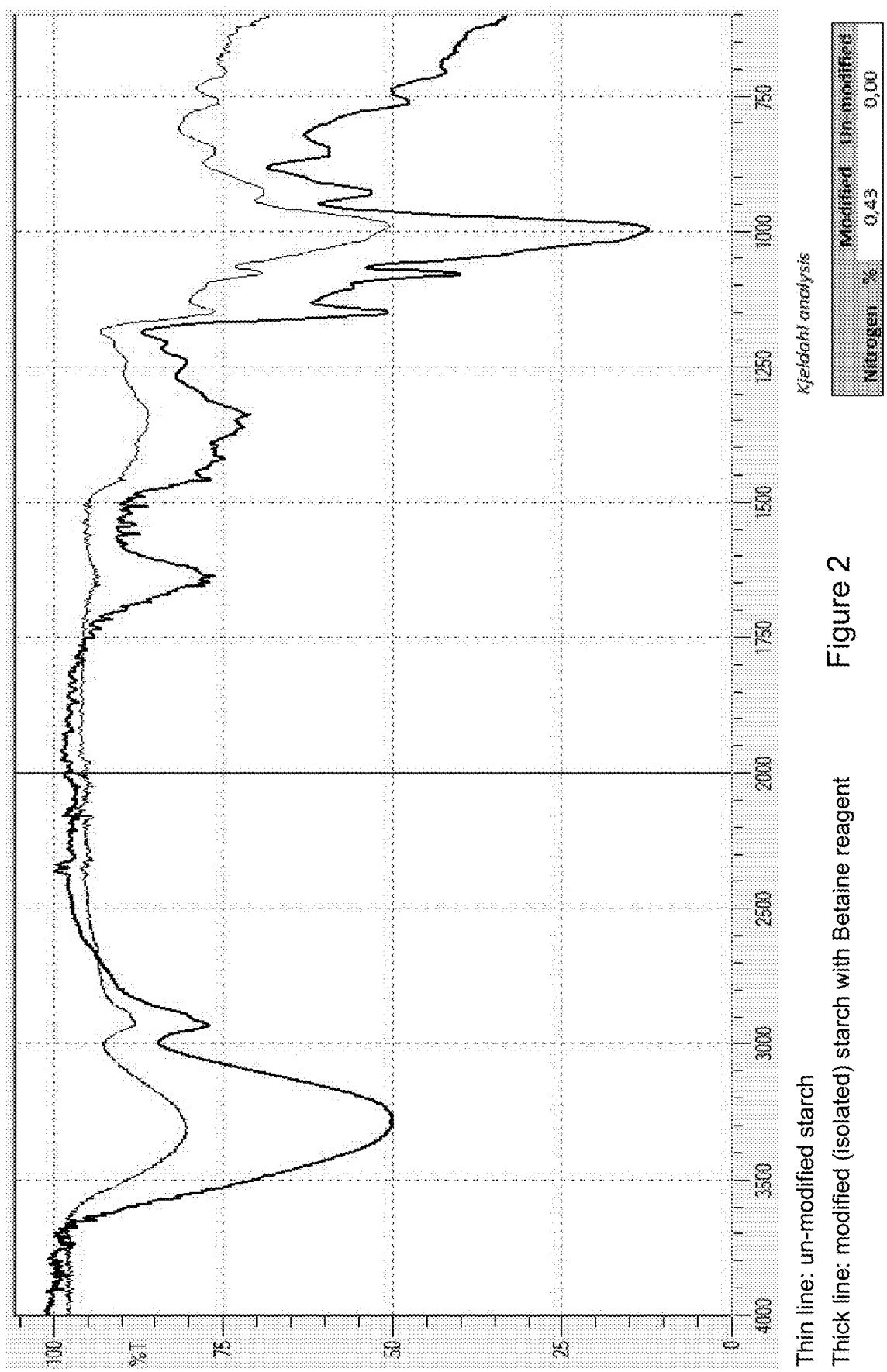
FIG. 2 shows overlapping FTIR scans for an unmodified starch and a starch modified with a compound having Formula (I) made from betaine, according to an embodiment of the present invention.

FIG. 2 shows overlapping FTIR scans for an unmodified starch and a starch modified with a compound having Formula (I) made from betaine to form a cationic starch, according to an embodiment of the present invention. As shown, the Kjeldahl nitrogen analysis shows the incorporation of the N atom from the betaine-source cationization reagent in the starch modified according to the present invention. The differences in the IR peaks show the characteristic peaks for the unmodified starch, as compared to the IR peaks for the starch modified according to an embodiment of the present invention. It is noted, for example, that the peak at about 1650 cm-1 would correspond to the C—N bonds in the betaine reagent added to the (poly)saccharide.

Figure 3:
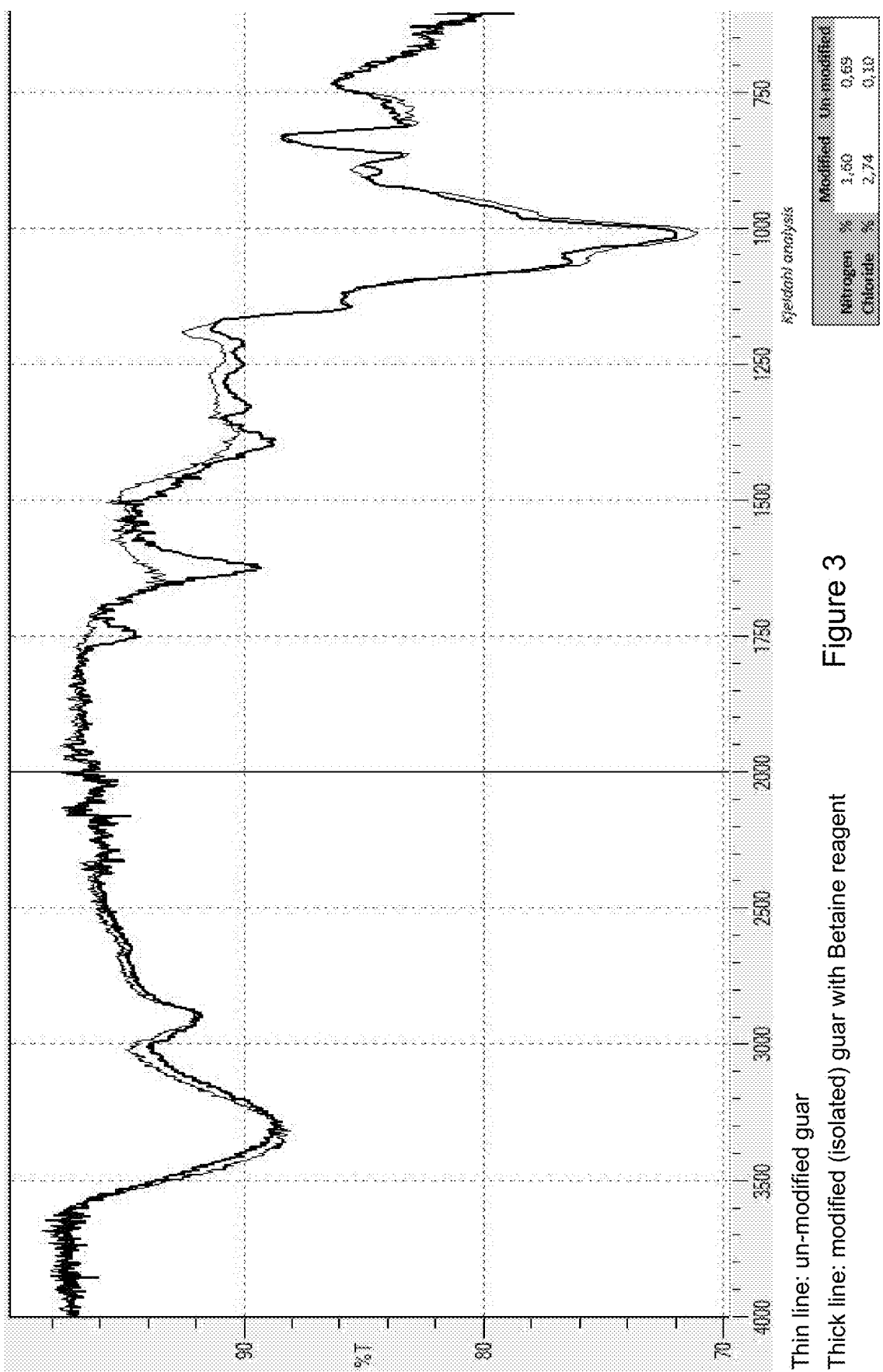
FIG. 3 shows overlapping FTIR scans for an unmodified guar and a guar modified with a compound having Formula (I) made from betaine, according to an embodiment of the present invention.

FIG. 3 shows overlapping FTIR scans for an unmodified guar and a guar modified with a compound having Formula (I) made from betaine, according to an embodiment of the present invention. As shown, the Kjeldahl nitrogen analysis shows the incorporation of the N atom from the betaine-source cationization reagent in the guar modified according to the present invention. The differences in the IR peaks show the characteristic peaks for the unmodified guar, as compared to the IR peaks for the guar modified according to an embodiment of the present invention. It is noted, for example, that the peak at about 1750 cm-1 would correspond to the ester carbonyl group.

Figure 4:
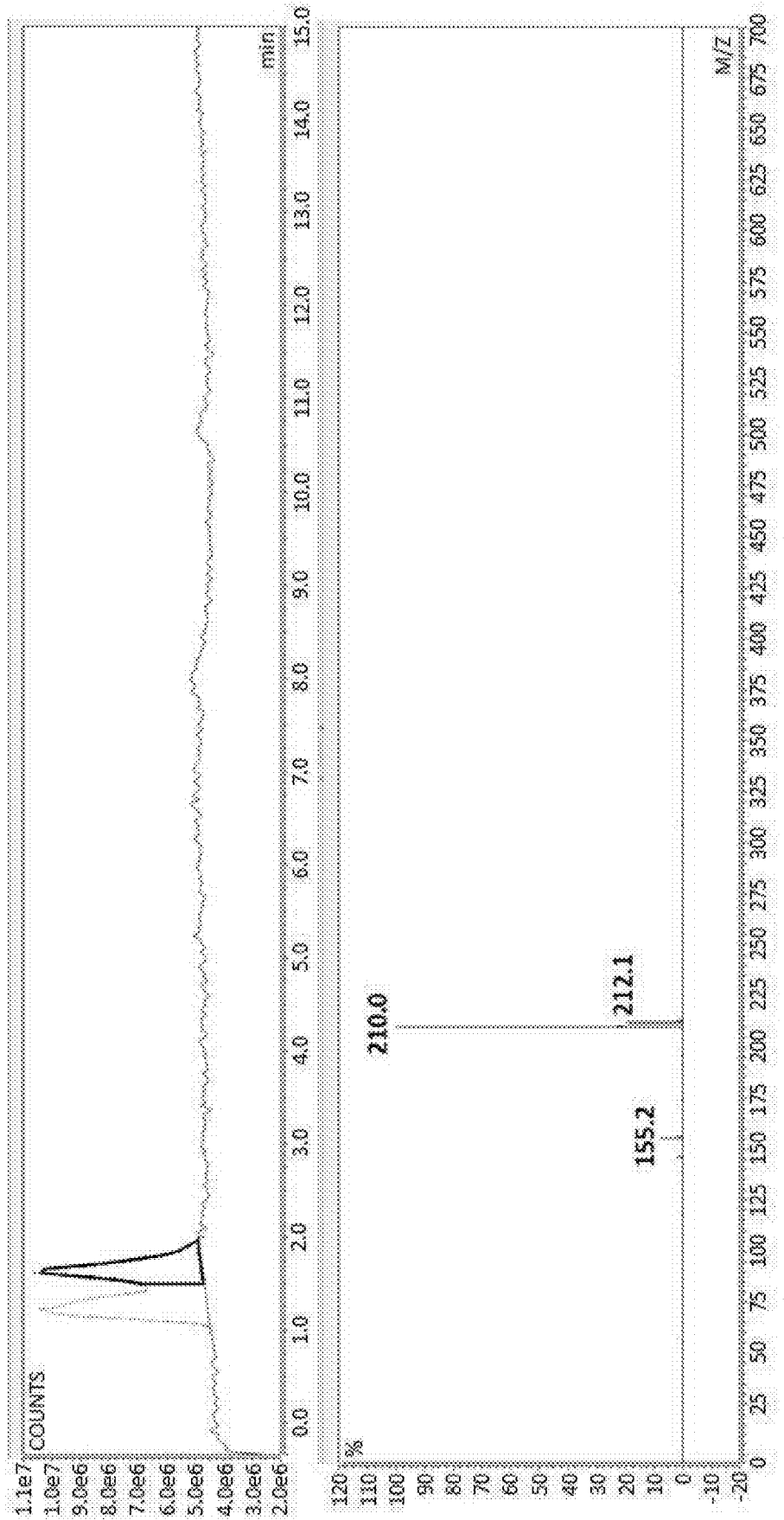
FIG. 4 shows a mass spectra for a betaine reagent having Formula (I) made from betaine, according to an embodiment of the present invention.

FIG. 4 shows a mass spectra for a betaine reagent having Formula (I) made from betaine, according to an embodiment of the present invention. As shown, the cationic betaine-derived Betain REAGENS™ has molecular weight of 209.68, and the MS spectrum shows a prominent peak at 210, corresponding to the Betaine REAGENS™ cation plus a proton.

It is noted that, throughout the specification and claims, the numerical limits of the disclosed ranges and ratios may be combined, and are deemed to include all intervening values. Furthermore, all numerical values are deemed to be preceded by the modifier "about", whether or not this term is specifically stated. Unless otherwise specified, all pressures are atmospheric and all temperatures are room temperature (about 20° C. to about 25° C.).

Furthermore, it should be appreciated that the process steps and structures described herein do not form a complete process flow for manufacturing products such as those described herein. The present invention can be practiced in conjunction with synthetic techniques currently used in the art, and only so much of the commonly practiced process steps are included as are necessary for an understanding of the present invention.

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

What is claimed is:

1. A compound having Formula (I) or Formula (II):

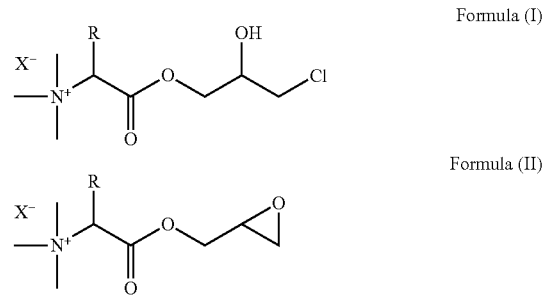

Formula (I)

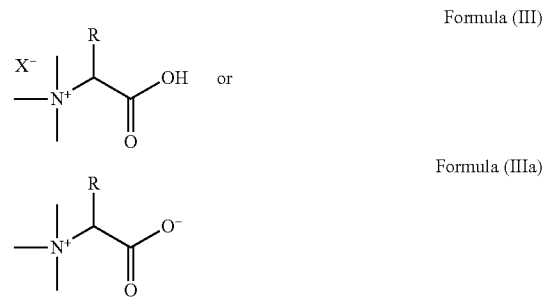

Formula (II)

or a mixture of both a compound having Formula (I) and a compound having Formula (II), wherein R is —H; —CH$_3$; —CH—(CH$_3$)$_2$; —CH$_2$—CH—(CH$_3$)$_2$; —CH—(CH$_3$)—CH$_2$—CH$_3$; —CH$_2$—(C$_6$H$_5$); —CH$_2$-(3-indole); —CH$_2$—CH$_2$—S—CH$_3$; —CH$_2$—OH; —CH—(CH$_3$)—OH; —CH$_2$—SH; —CH$_2$-(p-C$_6$H$_4$OH); —CH$_2$—CH$_2$—CH$_2$—CH$_2$—NH$_2$; —CH$_2$—CO—NH$_2$; —CH$_2$—CH$_2$—CO—NH$_2$; —CH$_2$—CH$_2$—COOH; —CH$_2$—COOH; or —CH$_2$—CH$_2$—NH—C=NH$_2$(NH$_2$);

and X is an anion.

2. A process for producing the compound having Formula (I) as defined in claim 1, comprising:

providing a first compound having either Formula (III) or Formula (IIIa):

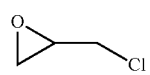

Formula (III)

Formula (IIIa)

wherein R and X are as defined in claim 1;

providing epichlorohydrin, having formula:

or providing 1,3-dichloro-2-propanol, having formula:

ClCH$_2$—CH(OH)—CH$_2$Cl or providing a mixture of both epichlorohydrin and 1,3-dichloro-2-propanol; and reacting the first compound with the epichlorohydrin or the 1,3-dichloro-2-propanol or the mixture of epichlorohydrin and 1,3-dichloro-2-propanol under suitable esterification conditions to form the compound having Formula (I).

3. A process for producing the compound having Formula (II) as defined in claim 1, comprising:
providing a first compound having either Formula (III) or Formula (IIIa):

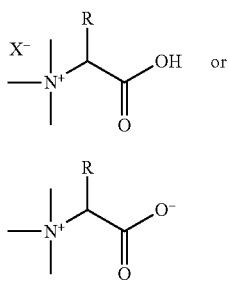

wherein R and X are as defined in claim 1;
providing epichlorohydrin, having formula:
or

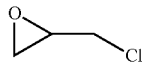

providing 1,3-dichloro-2-propanol, having formula:

or
providing a mixture of both epichlorohydrin and 1,3-dichloro-2-propanol;
reacting the first compound with the epichlorohydrin or the 1,3-dichloro-2-propanol or the mixture of epichlorohydrin and 1,3-dichloro-2-propanol under suitable esterification conditions to form the compound having Formula (I), and
converting the compound having Formula (I) to the compound having Formula (II) by an epoxidation reaction.

4. A cationic (poly)saccharide comprising a reaction product of the compound having the Formula (I) or the compound having the Formula (II) or a mixture of both the compound having Formula (I) and the compound having Formula (II) of claim 1 with a (poly)saccharide, wherein the (poly)saccharide is a starch, a guar, or a cellulose.

5. The cationic (poly)saccharide according to claim 4, wherein the cationic (poly)saccharide comprises the reaction product made with the compound having Formula (I).

6. The cationic (poly)saccharide according to claim 4, wherein the cationic (poly)saccharide comprises the reaction product made with the compound having Formula (II).

7. The cationic (poly)saccharide according to claim 4, wherein the cationic (poly)saccharide comprises the reaction product made with the mixture of both the compound having Formula (I) and the compound having Formula (II).

8. A process for producing a cationic (poly)saccharide comprising:
providing a suitable (poly)saccharide;
providing the compound having Formula (I) or the compound having Formula (II) or a mixture of both the compound having Formula (I) and the compound having Formula (II) as defined in claim 1;
reacting the suitable (poly)saccharide with the compound having Formula (I) or the compound having Formula (II) or the mixture of both the compound having Formula (I) and the compound having Formula (II) under suitable conditions to result in reaction to form the cationic (poly)saccharide.

9. The process according to claim 8, wherein the (poly)saccharide is a starch, a guar, or a cellulose.

10. The process according to claim 8 wherein the cationic (poly)saccharide comprises the reaction product made with the compound having Formula (I).

11. The process according to claim 9 wherein the cationic (poly)saccharide comprises the reaction product made with the compound having Formula (I).

12. The process according to claim 8 wherein the cationic (poly)saccharide comprises the reaction product made with the compound having Formula (II).

13. The process according to claim 9 wherein the cationic (poly)saccharide comprises the reaction product made with the compound having Formula (II).

14. The process according to claim 8 wherein the cationic (poly)saccharide comprises the reaction product made with the mixture of both the compound having Formula (I) and the compound having Formula (II).

15. The process according to claim 9 wherein the cationic (poly)saccharide comprises the reaction product made with the mixture of both the compound having Formula (I) and the compound having Formula (II).

* * * * *